(12) United States Patent
Harris et al.

(10) Patent No.: US 7,022,700 B2
(45) Date of Patent: Apr. 4, 2006

(54) METHOD OF INCREASING NEUTROPHIL PRODUCTION USING OPTICALLY-PURE (R)-2,3-BENZODIAZEPINES

(75) Inventors: Herbert W. Harris, Merion, PA (US); Robert F. Kucharik, Glenmoore, PA (US)

(73) Assignee: Vela Pharmaceuticals, Inc., Ewing, NJ (US)

( * ) Notice: Subject to any disclaimer, the term of this patent is extended or adjusted under 35 U.S.C. 154(b) by 172 days.

(21) Appl. No.: 10/309,527

(22) Filed: Dec. 3, 2002

(65) Prior Publication Data

US 2004/0106601 A1 Jun. 3, 2004

(51) Int. Cl.
*A61K 31/55* (2006.01)
*A61K 31/553* (2006.01)

(52) U.S. Cl. .............. 514/221; 514/211.13; 514/218

(58) Field of Classification Search ............. 514/221, 514/211.13, 218, 183, 30, 924
See application file for complete search history.

(56) References Cited

U.S. PATENT DOCUMENTS

| | | | | |
|---|---|---|---|---|
| 3,736,315 A | 5/1973 | Kórósi et al. | ............. | 540/567 |
| 4,322,346 A | 3/1982 | Kórósi et al. | ............. | 540/567 |
| 4,423,044 A | 12/1983 | Kórósi et al. | ............. | 514/221 |
| 4,614,740 A | 9/1986 | Láng et al. | ............. | 514/221 |
| 4,835,152 A | 5/1989 | Kórósi et al. | ............. | 514/220 |
| 4,840,948 A | 6/1989 | Láng et al. | ............. | 514/221 |
| 5,204,343 A | 4/1993 | Andrási et al. | ............. | 514/221 |
| 5,288,863 A | 2/1994 | Somogyi et al. | ............. | 540/567 |
| 5,451,700 A | 9/1995 | Morrissey | ............. | 564/165 |
| 5,459,137 A | 10/1995 | Andrási et al. | ............. | 514/220 |
| 5,519,019 A | 5/1996 | Andrási et al. | ............. | 514/220 |
| 5,521,174 A | 5/1996 | Andrási et al. | ............. | 514/220 |
| 5,639,751 A | 6/1997 | Andrási et al. | ............. | 514/220 |
| 5,891,871 A | 4/1999 | Xia et al. | ............. | 514/219 |
| 6,075,018 A | 6/2000 | Vágó et al. | ............. | 514/221 |
| 6,080,736 A | 6/2000 | Landry | ............. | 514/221 |

FOREIGN PATENT DOCUMENTS

| | | |
|---|---|---|
| EP | 0 492 485 A1 | 7/1992 |
| HU | 178516 | 3/1983 |
| WO | WO 92/11262 | 7/1992 |
| WO | WO 00/24400 | 5/2000 |

OTHER PUBLICATIONS

R. J. Griffiths et al., "Leukotriene $B_4$ Plays a Critical Role in the Progression of Collagen-Induced Arthritis", Proc. Natl. Acad. Sci. USA, vol. 92, pp. 517-521, Jan. 1995, Medical Sciences.

F. Gatta et al., "Derivatives of 2,3-Benzodiazepine (*)", Il Farmaco—Ed. Sc.—vol. 40—fasc. 12, pp. 942-955.

R. Sladká et al., "A Placebo-controlled Clinical Trial with Tofizopam * in the Treatment of Anxiety Neurosis" Divisions of Psychiatry, District Institutes of National Health, Prague, 2 and 4; Psychiatric Department and Psychiatric Research Unity, Medical Scholl of Charles University, Prague, Czechoslovakia, pp. 176-180.

Edit J. Horváth et al., "Anxiolytic 2,3-benzodiazepines, their Specific Binding to the Basal Ganglia", Progress in Neurobiology vol. 60 (2000), pp. 309-342.

E. Tomori et al., "Investigation of the Metabolites of Tofizopam in Man and Animals by Gas-Liquid Chromatography-Mass Spectrometry", Journal of Chromatography, 241 (1982), pp. 89-99.

Eva Tomori et al., "Investigation of Metabolites of Tofizopam in Man and Animals", Polish Journal of Pharmacology and Pharmacy, 1984, 36, pp. 423-430., PL ISSN 0301-0214.

Sharon Pellow et al., "The Effects of Tofisopam, a 3,4-Benzodiazepine, in Animal Models of Anxiety, Sedation, and Convulsions", Drug Development Research 7, pp. 61-73 (1986).

(Continued)

*Primary Examiner*—Kevin E. Weddington
(74) *Attorney, Agent, or Firm*—Drinker Biddle & Reath LLP; Daniel A. Monaco

(57) ABSTRACT

Compounds according to formula I:

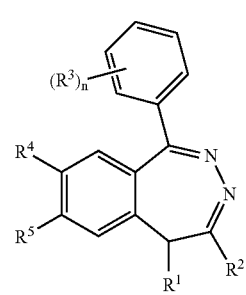

wherein $R^1$, $R^2$, $R^3$, $R^4$, $R^5$ and n are as defined herein, are administered to increase neutrophil levels in mammals.

1 Claim, No Drawings

OTHER PUBLICATIONS

A. Bond et al., "A Comparison of the Psychotropic Profiles of Tofisopam and Diazepam", Fur J Clin Pharmacol (1982) 22, pp. 137-142.

B.S. Tsai et al., "The Leukotriene $B_4$ Receptor Agonist/Antagonist Activities of SC-45694 in Human Neutrophils", The Journal of Pharmacology and Experimental Therapeutics, vol. 268, No. 3, 1994, pp. 1493-1498.

Noal Cohen et al., "Recent Progress in the Development of Leukotriene $B_4$ Antagonists", Curr. Opin. Invest. Drugs (1994), 3(1), pp. 13-22.

J. Kanto et al., "Tofizopam: A Benzodiazepine Derivative Without Sedative Effect", International Journal of Clinical Pharmacology, Therapy and Toxicology, vol. 20 No. 7—1982, pp. 309-312.

T. Mennini et al., "Brain Levels of Tofizopam in the Rat and Relationship with Benzodiazepine Receptors", Naunyn-Schmiedeberg's Arch Pharmacol (1982) 321, pp. 112-115.

K. Maier et al., "The Effect of Tofisopam on Psychic Performance in Persons with More than Average Anxiety: A Controlled Experimental Trial", Current Therapeutic Research, vol. 35, No. 4, Apr. 1984, pp. 541-548.

Chihiro Ito, Behavioral Pharmacological Study of the Structure-Activity Relationship of Benzodiazepine Derivatives—with Particular Reference to the Activity of 2,3-Benzodiazepine-, (1981) 39(3), pp. 369-384 (Japanese), pp. 1-30 (English Translation).

Milena Rizzo, "Chromatographic Separation of 2, 3-Benzodiazepines", Journal of Chromatography B, 747 (2000), pp. 203-216.

Miklos Simonyi et al, "Stereoselective Binding of a 2,3-Benzodiazepine to Human Serum Albumin", Biochemical Pharmacology, vol. 32, No. 12, (1983), pp. 1917-1920.

Giovambattista De Sarro et al., "GYKI 52466 and Related 2,3-Benzodiazepines as Anticonvulsant Agents in DBA/2 Mice", European Journal of Pharmacology 294 (1995), pp. 411-422.

T. Seppälä, "Tofisopam, A Novel 3,4-Benzodiazepine: Multiple-Dose Effects on Psychomotor Skills and Memory. Comparison with Diazepam and Interactions with Ethanol", Psychopharmacology 69, (1980), pp. 209-218.

Veijo Saano et al., "Tofisopam Modulates the Affinity of Benzodiazepine Receptors in the Rat Brain", Pharmacology Biochemistry & Behavior, vol. 17, (1982), pp. 367-369.

Sharon Pellow et al., "The Effects of Tofisopam, a 3,4-Benzodiazepine, in Animal Models of Anxiety, Sedation, and Convulsions", Drug Development Research 7 (1986), pp. 61-73.

A. Pakkanen et al., "Comparative Study of the Clinical Effects of Tofizopam, Nitrazepam and Placebo as Oral Premedication", British Journal of Anacsthesics, pp. 1009-1012.

V. Saano et al., "Tofizopam Enhances the Action of Diazepam Against Tremor and Convulsions", Medical Biology 61: (1983), pp. 49-53.

V. Saano et al., "Tofizopam Selectively Increases the Action of Anticonvulsants", Medical Biology, 64 (1986), pp. 201-206.

S. Nicosia et al., "Leukotrienes as Mediators of Asthma", Pulmonary Pharmacology & Therapeutics, (2001) 14, pp. 3-19.

Daniel W. Goldman et al. "Transduction by Leukotriene $B_4$ Receptors of Increases in Cytosolic Calcium in Human Polymorphonuclear Leukocytes", vol. 35, No. 1, Jul. 1985, pp. 525-530.

Julia Visy et al., "The Role of Configuration and Conformation in the Binding of 2,3-Benzodiazepines to Human Serum Albumin", CHIRALITY 1 (1989), pp. 271-275.

István Tarnawa et al., "Structure-Activity Relationships of 2,3-Benzodiazepine Compounds with Glutamate Antagonistic Action", Bioorganic & Medical Chemistry Letters, vol. 3, No. 1, (1993), pp. 99-104.

Sergey V. Kalashnikov et al., "Immunomodulating Effects of Tofizopam (Grandaxin®) and Diazepam in Vitro", Mediators of Inflammation, vol. 11, (2002), pp. 53-59.

Fogassy E. et al., "Studies on the Properties and Structure of Optically Active 1-(3,4-Dimethoxyphenyl)-4-Methyl-5-Ethyl-7,8-Dimethoxy-5H-2,3-Benzodiazepine (Tofizopam)", Studies in Organic Chemistry, vol. 18, (1984), pp. 229-233.

K. Yamaguchi et al., "Tofisopam, A New 2,3-Benzodiazepine. Inhibition of Changes Induced by Stress Loading and Hypothalamic Stimulation", Can. J. Physiol Pharmaco, vol. 61, (1983), pp. 619-625.

Szegó Judit et al., "Selected Passages From the Clinical-Pharmacological and Clinical Trials of Grandaxin®, " Acta Pharmaceutica Hungarica vol. 63, (1993), pp. 91-98 (Hungarian). pp. 1-10 (English Translation).

L. Petócz et al., The Main Pharmacological Characteristics of Grandaxin (Tofizopam, Egyt-341), Hungarian Medical Journal, vol. 23, No. 4, (1975), pp. 134-138.

Petócz Luijza, "The Pharmacological Effects of Tofizopam (Grandaxin)®", Acta Pharmaceutica Hungarica, vol. 63, (1993), pp. 79-82 (Hungarian. pp. 1-4 (English Translation).

METHOD OF INCREASING NEUTROPHIL PRODUCTION USING OPTICALLY-PURE (R)-2,3-BENZODIAZEPINES

FIELD OF THE INVENTION

The present invention relates to the use of 2,3-benzodiazepines in increasing neutrophil production in mammals.

BACKGROUND OF THE INVENTION 2,3-Benzodiazepines

Certain 2,3-benzodiazepines have been explored extensively for their potent CNS modulating activity. Compounds such as tofisopam (Grandaxin®), girisopam, and norisopam (structures shown below with the atom numbering system indicated for tofisopam) have demonstrated substantial anxiolytic and antipsychotic activity.

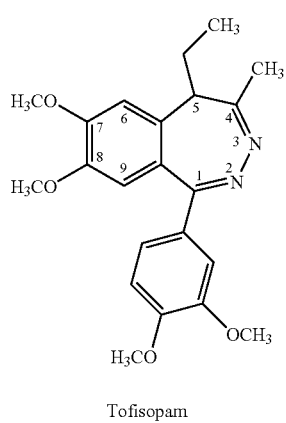

Tofisopam

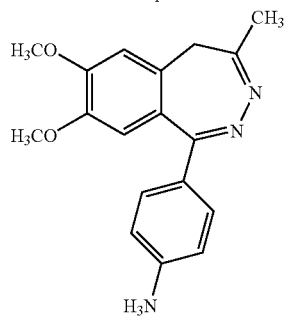

Nerisopam

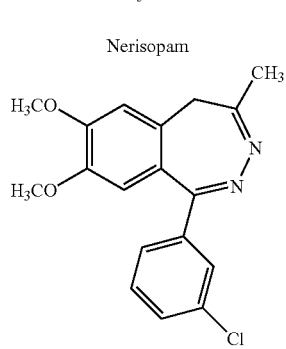

Girisopam

Tofisopam has been shown in humans to have an activity profile that is significantly different from that of widely used 1,4-benzodiazepine (BZ) anxiolytics such as diazepam (Valium®) and chlordiazepepoxide (Librium®). The 1,4-benzodiazepines, in addition to having sedative-hypnotic activity, also possess muscle relaxant and anticonvulsant properties that, though therapeutically useful in some disease states, are nonetheless potentially untoward side effects. Thus, the 1,4-benzodiazepines, though safe when administered alone, may be dangerous in combination with other CNS drugs including alcohol.

Tofisopam, in contrast, is a non-sedative anxiolytic that has no appreciable sedative, muscle relaxant or anticonvulsant properties. See Horvath et al., *Progress in Neurobiology*, 60 (2000), 309–342; the entire disclosure of which is incorporated herein by reference. In clinical studies, tofisopam improved rather than impaired psychomotor performance and showed no interaction with ethanol (Id.). These observations comport with data that show that tofisopam does not interact with central benzodiazepine (BZ) receptors and binds only weakly to peripheral BZ receptors. Additional studies have shown that tofisopam enhances mitogen-induced lymphocyte proliferation and IL-2 production in vitro. (Id)

Other 2,3-benzodiazepines, though structurally similar to tofisopam, have been investigated and shown to have varying activity profiles. For example, GYKI-52466 and GYKI-53655 (structures shown below) act as noncompetitive glutamate antagonists at the AMPA (α-amino-3-hydroxy-5-methyl-4-isoxazolepropionic acid) site, and have demonstrated neuroprotective, muscle relaxant and anticonvulsant activity (Id.). Another group of 2,3-benzodiazepines that have been investigated are represented by the compound GYKI-52895, and show activity as selective dopamine uptake inhibitors with potential use in antidepressant and anti-Parkinsonism therapy (Id.).

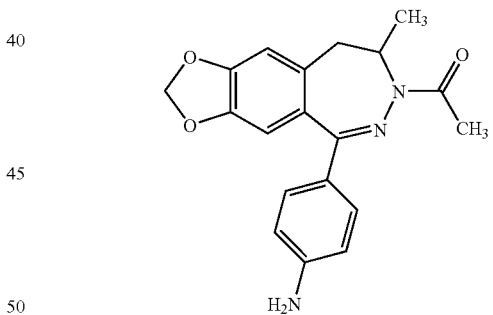

GKY-53655

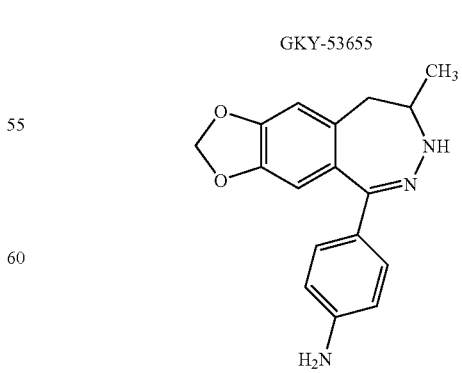

GKY-52895

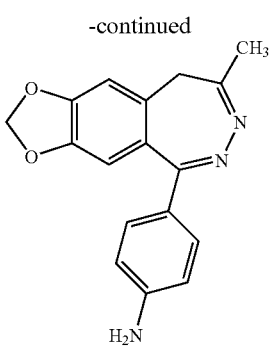

GKY-52466

Tofisopam is a racemic mixture of (R)- and (S)-enantiomers. This is due to the asymmetric carbon, i.e., a carbon with four different groups attached, at the 5-position of the benzodiazepine ring. The molecular structure and conformational properties of tofisopam have been determined by NMR, CD and x-ray crystallography (Visy et al., *Chirality* 1:271–275 (1989)). The 2,3-diazebine ring exists as two different conformers. The major conformers, (+)R and (−)S have the 5-ethyl group in a quasi-equatorial position, while in the minor conformers, (−)R and (+)S, the 5-ethyl group is positioned quasi-axially. Thus, racemic tofisopam can exist as four molecular species, i.e., two enantiomers, each of which exists as two conformations. The sign of the optical rotation is reversed upon inversion of the diazepine ring from one conformer to the other. In crystal form, tofisopam exists only as the major conformations, with dextrorotatory tofisopam being of the (R) absolute configuration. (Toth et al., *J. Heterocyclic Chem.*, 20:709–713 (1983); Fogassy et al., *Bioorganic Heterocycles*, Van der Plas, H. C., Ötvös, L, Simongi, M., eds. Budapest Amsterdam: Akademia; Kiado-Elsevier, 229:233 (1984)).

Differential binding of these two conformations of tofisopam has been reported in binding studies with human albumin (Simongi et al. *Biochem. Pharm.*, 32(12), 1917–1920, 1983). The two conformers have also been reported as existing in equilibrium (Zsila et al., *Journal of Liquid Chromatography & Related Technologies*, 22(5), 713–719, 1999; and references therein).

The optically pure (R)-enantiomer of tofisopam (R)-1-(3,4-dimethoxyphenyl)-4-methyl-5-ethyl-7,8-dimethoxy-5H-2,3-benzodiazepine) has been isolated and shown to possess the nonsedative anxiolytic activity of the racemic mixture. See U.S. Pat. No. 6,080,736; the entire disclosure of which is incorporated herein by reference.

Neutropenia

Neutrophils, also called polymorphonuclear leukocytes, are the most numerous of the blood cells known as granulocytes. Neutrophils are the largest cell population involved in acute inflammatory response. They are thus an important component of natural immunity, responding quickly to chemotactic stimuli. Neutrophils destroy foreign particles such as bacteria by enveloping and digesting them, a process called phagocytosis. Neutrophils increase in response to bacterial infection. When many neutrophils are needed, they are released from the bone marrow as immature cells, called bands or stab cells.

Neutropenia is a blood disorder wherein the number of neutrophils in the blood is abnormally low as assessed by an Absolute Neutrophil Count (ANC). An ANC is acquired by performing a differential blood cell count in which percentages of cell types are recorded as well as the total number of cells. The differential blood cell count is done by spreading a drop of blood on a microscope slide. The slide is stained and examined under a microscope. One hundred white cells are counted and identified as either neutrophils, bands, lymphocytes, monocytes, eosinophils or basophils. Any a typical or immature cells also are counted. Cells are identified by the shape and appearance of the nucleus, the color of cytoplasm (the background of the cell), and the presence and color of granules. The percentage of each cell type is reported. Some instruments may be used to perform an automated differential.

A neutrophil shortage corresponds to an increased risk of microbial infection. The blood of healthy human adults contains about 2500 to 6000 neutrophils per $mm^3$. In children under the age of six, the count may be lower. Various sources have set the threshold for the diagnosis of neutropenia at different measured neutrophil levels ranging from an ANC of about 2000 neutrophils per mm to about 1500 neutrophils per $mm^3$. See The Merck Manual $17^{th}$ Ed. 1999, Section 11, Chapter 135, and Wallner, et al., U.S. Pat. No. 6,300,314, Oct. 9, 2001, the entire disclosures of which are incorporated herein by reference. Severe neutropenia is diagnosed when the ANC falls below 500 neutrophils per $mm^3$. The symptoms, of increased risk of infection depend on the severity of the neutropenia and on the duration of the disorder.

Neutropenia treatable by methods of the present invention may be a chronic disorder. Neutropenia as a chronic disorder may be further classified as congenital, cyclical and idiopathic neutropenia. Chronic congenital neutropenia is inherited by a small number of individuals. The most severe form of congenital neutropenia is Kostmann's Syndrome and there are other, milder variations. Symptoms include frequent infections and fevers.

Cyclical neutropenia results from a regulatory defect at the hematopoietic stem cell level that causes oscillations in production of neutrophils as well as other types of blood cells. Individuals with this disorder will have neutrophil counts of about 100 neutrophils per $mm^3$ for three to six days out of every cycle. The neutrophil count ranges from severe to moderate neutropenia levels through most of the cycle.

Chronic idiopathic neutropenia refers to severe chronic neutropenia that does not clearly fall into either of the above classifications. Individuals suffering from chronic idiopathic neutropenia typically acquire the disorder after having normal neutrophil counts earlier in life. It is estimated that neutropenia may occur as a congenital or idiopathic disorder in an estimated frequency of one per 200,000 in the population.

Neutropenia may also occur secondary to another condition such as cancer or Acquired Immunodeficiency Syndrome. Neutropenia may also occur secondary to an event such as a drug therapy. Thus, neutropenia may result from physiological disorders that directly affect the immune system. For example, diminished neutrophil production will result when leukemia, myeloma, lymphoma or a metastatic solid tumor such as, for example, breast or prostate cancer, infiltrate and replace bone marrow. Transient neutropenia is often associated with viral infections. Chronic neutropenia is often associated with immunodeficiency resulting from a viral infection, for example, Acquired Immunodeficiency Syndrome (AIDS) resulting from infection with Human Immunodeficiency Virus (HIV). Autoimmune neutropenia may be associated with circulating antineutrophil antibodies.

A much more common cause is neutropenia as a side effect of drug therapy, particularly cancer chemotherapy, radiation therapy for cancer and bone marrow transplantation associated with cancer therapy. Neutropenia secondary to drug therapy can thus be subdivided into two groups. The first involves immune-mediated neutropenia that may arise from drugs that act as haptens to stimulate antibody formation. Acute hypersensitivity reactions such as those caused by diphenylhydantoin and phenobarbital may last a few days. However, chronic hypersensitivity reactions may last for months or years. See The Merck Manual, 17th Ed., Id.

The second area of drug-induced neutropenia involves the severe neutropenia that predictably occurs after large doses of cytoreductive cancer drugs and which also accompanies ionizing radiation therapy. These cytotoxic therapies induce neutropenia because of the proliferative nature of neutrophil precursor cells and the normal rapid turnover rate of circulating neutrophils. See The Merck Manual, 17th Ed., Id. The risk of neutropenia secondary to cancer chemotherapy or radiotherapy depends on the type and stage of the cancer and the type, the dosage and the schedule of cancer treatment. Approximately 1.4 million cancer patients in the US received chemotherapy in 2001. About one half of chemotherapy patients develop neutropenia. At present, less than 10% of chemotherapy patients receive prophylactic treatment to prevent neutropenia.

Therapy that exists currently for raising neutrophil levels consists primarily of filgrastim (Nupogen®) and more recently, pegfilgrastim (Neulasta™), a longer acting derivative of filgrastim. Filgrastim is a recombinant version of a human protein, G-CSF (granulocyte-colony stimulating factor), that selectively stimulates the production of white blood cells. G-CSF is currently the drug of choice for neutropenia. Since both of these drugs are recombinant proteins they are not active orally and must be administered by injection. In addition, protein-based drugs are often subject to rapid metabolism. The elimination half-life of Nupogen® is 3.5 hours and of Neulasta™ is in the range of 15–80 hours.

New agents are needed which are useful in the treatment of neutropenia. In particular, agents are needed that demonstrate biological activity when administered via routes other than injection. Particularly, agents that may be orally active are needed, as they may serve to enhance patient compliance.

SUMMARY OF THE INVENTION

In one embodiment of the invention there is provided a method of increasing the absolute neutrophil count in an individual, comprising administering to the individual an effective amount of at least one compound according to formula I:

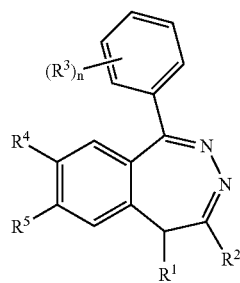

I wherein:

$R^1$ is —$(C_1-C_7)$hydrocarbyl or —$(C_2-C_6)$heteroalkyl;

$R^2$ is selected from the group consisting of —H, and —$(C_1-C_7)$hydrocarbyl, wherein $R^1$ and $R^2$ may combine to form a carbocyclic or heterocyclic 5- or 6-membered ring;

$R^3$ is independently selected from the group consisting of —O$(C_1-C_6)$alkyl, —OH, —O-acyl, —SH, —S$(C_1-C_3)$alkyl, —NH$_2$, —NH$(C_1-C_6)$alkyl, —N$((C_1-C_6)$alkyl$)_2$, —NH-acyl, —NO$_2$ and halogen;

n is 1, 2 or 3;

$R^4$ and $R^5$ are independently selected from the group consisting of —O$(C_1-C_6)$alkyl, —OH, O-acyl, —SH, —S$(C_1-C_3)$alkyl, —NH$_2$, NH-acyl and halogen, wherein $R^4$ and $R^5$ may combine to form a 5, 6 or 7-membered heterocyclic ring; or a pharmaceutically-acceptable salt of such a compound;

wherein the administered compounds according to formula I comprise an R-enantiomer with respect to the absolute conformation at the 5-position of the benzodiazepine ring, and is substantially free of the corresponding S-enantiomer of the same compound.

Preferably, the administered compound of formula I, or a pharmaceutically-acceptable salt of such a compound, comprises 85% or more by weight of the (R)-enantiomer. More preferably, administered compound of formula I, or a pharmaceutically-acceptable salt of such a compound, comprises 90% or more by weight of the (R)-enantiomer. Even more preferably, the administered compound of formula I, or a pharmaceutically-acceptable salt of such a compound, comprises 95% or more by weight of the (R)-enantiomer. Most preferably, the administered compound of formula I, or a pharmaceutically-acceptable salt of such a compound, comprises 99% or more by weight of the (R)-enantiomer.

According to another embodiment of the invention, there is provided a method of treating an individual afflicted with neutropenia, comprising administering to the individual an effective amount of a compound of formula I; wherein the administered compounds according to formula I comprise an R-enantiomer with respect to the absolute conformation at the 5-position of the benzodiazepine ring, and is substantially free of the corresponding S-enantiomer of the same compound.

According to another embodiment of the invention, there is provided a method of preventing neutropenia in an individual who is at risk of developing neutropenia, said method comprising administering to said individual an effective amount of at least one compound according to formula I; wherein the administered compounds according to formula I comprise an R-enantiomer with respect to the absolute conformation at the 5-position of the benzodiazepine ring, and is substantially free of the corresponding S-enantiomer of the same compound.

In a preferred embodiment of the administered compound:

$R^1$ is —$(C_1-C_6)$alkyl;

$R^2$ is selected from the group consisting of —H and —$(C_1-C_6)$alkyl;

$R^3$ is independently selected from the group consisting of —O$(C_1-C_6)$alkyl, —O-acyl and —OH;

n is 1, 2 or 3; and $R^4$ and $R^5$ are independently selected from —O$(C_1-C_6)$alkyl, —O-acyl and —OH, wherein, $R^4$ and $R^5$ may combine to form a 5, 6 or 7-membered heterocyclic ring; or a pharmaceutically-acceptable salt of such a compound.

According to another preferred embodiment of the administered compound:

R¹ is —CH₂CH₃;
R² is —C₁–C₆alkyl;
R³, R⁴ and R⁵ are independently selected from the group consisting of —OH and —OCH₃; and
n is 1, 2 or 3;
or a pharmaceutically-acceptable salt of such a compound.

According to a further preferred embodiment of the administered compound:

R¹ is —CH₂CH₃;
R² is —CH₃;
R³, R⁴ and R⁵ are independently selected from the group consisting of —OH and —OCH₃; and
n is 1, 2 or 3; or a pharmaceutically-acceptable salt of such a compound.

According to a further preferred embodiment of the administered compound:

R¹ is —CH₂CH₃;
R² is —CH₃;
R³, R⁴ and R⁵ are independently selected from the group consisting of —OH and —OCH₃; and
n is 2; or a pharmaceutically-acceptable salt of such a compound.

According to a further preferred embodiment of the administered compound:

R¹ is —CH₂CH₃;
R² is —CH₃;
R³, R⁴ and R⁵ are independently selected from the group consisting of —OH and —OCH₃;
n is 2; and wherein R³ comprises substituents at the 3- and 4-positions of the phenyl ring; or a pharmaceutically-acceptable salt of such a compound.

Preferably, compounds according to formula I, for administration, are selected from the group consisting of:

(R)-1-(3,4-dimethoxyphenyl)-4-methyl-5-ethyl-7,8-dimethoxy-5H-2,3-benzodiazepine;

(R)-1-(3,4-dimethoxyphenyl)-4-methyl-5-ethyl-7-hydroxy-8-methoxy-5H-2,3-benzodiazepine;

(R)-1-(3-hydroxy-4-methoxyphenyl)-4-methyl-5-ethyl-7,8-dimethoxy-5H-2,3-benzodiazepine;

(R)-1-(3-methoxy-4-hydroxyphenyl)-4-methyl-5-ethyl-7,8-dimethoxy-5H-2,3-benzodiazepine;

(R)-1-(3,4-dimethoxyphenyl)-4-methyl-5-ethyl-7-methoxy-8-hydroxy-5H-2,3-benzodiazepine;

(R)-1-(3-methoxy-4-hydroxyphenyl)-4-methyl-5-ethyl-7-hydroxy-8-methoxy-5H-2,3-benzodiazepine; and (R)-1-(3-hydroxy-4-methoxyphenyl)-4-methyl-5-ethyl-7-hydroxy-8-methoxy-5H-2,3-benzodiazepine; or a pharmaceutically-acceptable salt thereof.

More preferably, the compound according to formula I, for administration is (R)-1-(3,4-dimethoxyphenyl)-4-methyl-5-ethyl-7,8-dimethoxy-5H-2,3-benzodiazepine; or a pharmaceutically-acceptable salt thereof.

The compound, (R)-1-(3,4-dimethoxyphenyl)-4-methyl-5-ethyl-7,8-dimethoxy-5H-2,3-benzodiazepine, the R-enantiomer of tofisopam, is shown in the structure diagram below.

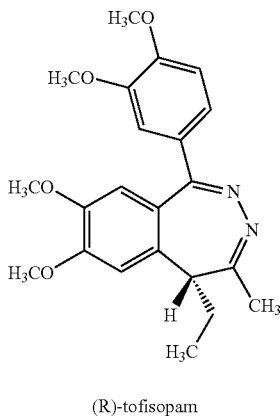

(R)-tofisopam

DEFINITIONS

The term "acyl" means a radical of the general formula —C(=O)—R, wherein —R is hydrogen, hydrocarbyl, amino, alkylamino, dialkylamino hydroxy or alkoxy. "Examples include for example, acetyl (—C(=O)CH₃), propionyl (—C(=O)CH₂CH₃), benzoyl (—C(=O)C₆H₅), phenylacetyl (—C(=O)CH₂C₆H₅), carboethoxy (—CO₂CH₂CH₃), and dimethylcarbamoyl (—C(=O)N(CH₃)₂). When the R group in the acetyl radical is alkoxy, alkyl amino or dialkyl amino, the alkyl portion is preferably (C₁–C₆)alkyl, more preferably (C₁–C₃)alkyl. When the R is hydrocarbyl, it is preferably (C₁–C₇)hydrocarbyl. When R is hydrocarbyl, it is preferably alkyl, more preferably (C₁–C₆)alkyl.

The term "alkyl", by itself or as part of another substituent means, unless otherwise stated, a straight, branched or cyclic chain hydrocarbon radical, including di- and multi-radicals, having the number of carbon atoms designated (i.e. C₁–C₆ means one to six carbons). Alkyl groups include straight chain, branched chain or cyclic groups, with straight being preferred. Examples include: methyl, ethyl, propyl, isopropyl, butyl, isobutyl, tert-butyl, pentyl, neopentyl, hexyl, cyclohexyl and cyclopropylmethyl. (C₁–C₆)alkyl is preferred. Most preferred is (C₁–C₃)alkyl, particularly ethyl, methyl and isopropyl.

The term "alkoxy" employed alone or in combination with other terms means, unless otherwise stated, an alkyl group having the designated number of carbon atoms, as defined above, connected to the rest of the molecule via an oxygen atom, such as, for example, methoxy, ethoxy, 1-propoxy, 2-propoxy (isopropoxy) and the higher homologs and isomers. Preferred are (C₁–C₆)alkoxy. More preferred is (C₁–C₃)alkoxy, particularly ethoxy and methoxy.

The term "amine" or "amino" refers to radicals of the general formula —NRR', wherein R and R' are independently selected from hydrogen or a hydrocarbyl radical, or wherein R and R' combined form a heterocycle. Examples of amino groups include: —NH₂, methyl amino, diethyl amino, anilino, benzyl amino, piperidinyl, piperazinyl and indolinyl. Preferred hydrocarbyl radicals are (C₁–C₇)hydrocarbyl radicals. Preferred are hydrocarbyl radicals that are alkyl radicals. More preferred are (C₁–C₆)alkyl.

The term "aromatic" refers to a carbocycle or heterocycle having one or more polyunsaturated rings having aromatic character (4n+2) delocalized π (pi) electrons).

The term "aryl" employed alone or in combination with other terms, means, unless otherwise stated, a carbocyclic aromatic system containing one or more rings (typically one, two or three rings) wherein such rings may be attached together in a pendent manner, such as a biphenyl, or may be fused, such as naphthalene. Examples include phenyl; anthracyl; and naphthyl.

The term "hydrocarbyl" refers to any moiety comprising only hydrogen and carbon atoms. This definition includes for example alkyl, alkenyl, alkynyl, aryl and benzyl groups. Preferred are ($C_1$–$C_7$)hydrocarbyl.

The term "heteroalkyl" by itself or in combination with another term means, unless otherwise stated, a stable straight or branched chain radical consisting of the stated number of carbon atoms and one or two heteroatoms selected from the group consisting of O, N, and S. Nitrogen and sulfur atoms may be optionally oxidized to the N-oxide and sulfoxide or sulfone, respectively. In addition, a nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group. Preferred are ($C_2$–$C_6$)heteroalkyl. More preferred are ($C_2$–$C_4$)heteroalkyl. Examples include: —O—$CH_2$—$CH_2$—$CH_3$, —$CH_2$—$CH_2CH_2$—OH, —$CH_2$—$CH_2$—NH—$CH_3$, —$CH_2$—C(=O)—$CH_3$, —$CH_2$—N=N—$CH_2$—$CH_3$, —$CH_2$—S—$CH_2$—$CH_3$, —$CH_2$—S(=O)—$CH_3$ and —$CH_2$—$CH_2$—NH—$SO_2$—$CH_3$. Up to two heteroatoms may be consecutive, such as, for example, —$CH_2$—NH—$OCH_3$, or —$CH_2$—$CH_2$—S—S—$CH_3$. More preferred are heteroalkyl groups containing one or two oxygen atoms.

When two groups may "combine to form a carbocyclic or heterocyclic 5- or 6-membered ring," a carbocyclic ring is preferably saturated. Preferred heterocyclic rings are saturated rings containing one or two heteroatoms selected from N, O and S. Heterocyclic rings annulated to the benzodiazepine seven-membered ring in this way include, for example, furan, dihydrofuran, tetrahydrofuran, pyran, dihydropyran, tetrahydropyran, thiophene, dihydrothiophene, tetrahydrothiophene, pyrrole, dihydropyrrole, pyrrolidine, pyridine, dihydropyridine, tetrahydropyridine and piperidine.

When two groups may "combine to form a 5-, 6- or 7-membered heterocyclic ring," preferred heterocyclic rings are 5- or 6-membered rings containing one or two heteroatoms selected from N, O and S. More preferred are heterocyclic rings containing one heteroatom selected from N, O and S. Heterocyclic rings annulated to the benzodiazepine phenyl ring in this way include, for example, furan, dihydrofuran, dioxane, dioxolane, pyran, dihydropyran, tetrahydropyran, thiophene, dihydrothiophene, pyridine, dihydropyridine, tetrahydropyridine, piperidine, pyrrole, dihydropyrrole, imidazole, dihydroimidazole, thiazole, dihydrothiazole, oxazole, and dihydrooxazole.

The term "substituted" means that an atom or group of atoms has replaced hydrogen as the substituent attached to another group. For aryl and heteroaryl groups, the term "substituted" refers to any level of substitution, namely mono-, di-, tri-, tetra-, or penta-substitution, where such substitution is permitted. The substituents are independently selected, and substitution may be at any chemically accessible position.

The phrase "optically active" refers to a property whereby a material rotates the plane of plane-polarized light. A compound that is optically active is nonsuperimposable on its mirror image. The property of nonsuperimposablity of an object on its mirror image is called chirality.

The property of "chirality" in a molecule may arise from any structural feature that makes the molecule nonsuperimposable on its mirror image. The most common structural feature producing chirality is an asymmetric carbon atom, i.e., a carbon atom having four nonequivalent groups attached thereto.

The term "enantiomer" refers to each of the two nonsuperimposable isomers of a pure compound that is optically active. Single enantiomers are designated according to the Cahn-Ingold-Prelog system, a set of priority rules that rank the four groups attached to an asymmetric carbon. See March, Advanced Organic Chemistry, $4^{th}$ Ed., (1992), p. 109. Once the priority ranking of the four groups is determined, the molecule is oriented so that the lowest ranking group is pointed away from the viewer. Then, if the descending rank order of the other groups proceeds clockwise, the molecule is designated R and if the descending rank of the other groups proceeds counterclockwise, the molecule is designated S. In the example below, the Cahn-Ingold-Prelog ranking sequence id A>B>C>D. The lowest ranking atom, D is oriented away from the viewer.

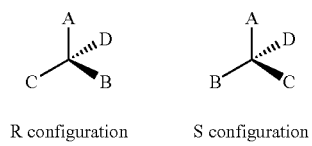

R configuration    S configuration

The term "racemate" or the phrase "racemic mixture" refers to a 50–50 mixture of two enantiomers such that the mixture does not rotate plane-polarized light.).

The term "substantially isolated", or "substantially free" of the other enantiomer or the term "resolved" or the phrase "substantially free" of the corresponding (S)-enantiomer, when used to refer to an optically active compound of formula I, means the (R)- and (S)-enantiomers of the compound have been separated such that the composition is 80% or more by weight a single enantiomer.

Thus, by "(R)-2,3-benzodiazepine substantially free of the (S)-enantiomer" is meant a 2,3-benzodiazepine compound that comprises 80% or more by weight of its (R)-enantiomer and likewise contains 20% or less of its (S)-enantiomer as a contaminant, by weight.

The phrase "effective amount" when used to describe therapy to an individual refers to an amount of a compound of formula I which results in increasing neutrophil production as measured by the absolute neutrophil count of the individual's blood. An effective amount of a compound of formula I for treatment of neutropenia is an amount which raises the absolute neutrophil count in an individual afflicted with neutropenia. An effective amount of a compound of formula I for the prevention of neutropenia is an amount which maintains the absolute neutrophil count of the individual above a level of about 500 neutrophils per $mm^3$ in an individual during a time interval coinciding with an increased risk of neutropenia. Conditions which are associated with an increased risk of neutropenia include, for example, a present or forthcoming regimen of cancer chemotherapy.

The term "individual" or "subject," includes human beings and non-human animals. With respect to the disclosed methods of increasing neutrophil production, these terms refer, unless the context indicates otherwise, to:

(a) an organism that is afflicted with a disorder characterized by neutropenia; or (b) an organism that is at increased risk for developing neutropenia, due, for example, to forthcoming cancer chemotherapy.

The selection of an individual at increased risk for developing neutropenia may take into account the presence of known risk factors. Such factors may include, for example, cancer requiring chemotherapy or therapeutic ionizing radiation; a disease that affects the immune system directly, such as for example Acquired Immunodeficiency Syndrome (AIDS); or the presence of a virus such as Human Immunodeficiency Virus (HIV) known to cause AIDS.

DETAILED DESCRIPTION OF THE INVENTION

According to the present invention, (R)-2,3-benzodiazepines of formula I, and pharmaceutically-acceptable salts thereof, may be used to increase neutrophil levels in an individual as measured by an absolute neutrophil count.

The use of compounds of formula I to raise neutrophil levels may be associated with one or more of several therapeutic goals. Therapy to raise neutrophil levels may treat neutropenia that exists as a primary disease state. Alternatively, therapy according to method of the invention may treat neutropenia that is secondary to another factor. Such factors include, for example, viral infection, cancer or therapy with a drug that causes neutropenia.

Therapy to raise neutrophil levels by methods of the present invention may also prevent neutropenia in instances wherein an individual is at risk of developing neutropenia. Such instances include, for example, an individual who anticipates beginning drug therapy using a drug known or suspected to cause neutropenia.

Numerous drugs have been shown to cause neutropenia as a side effect. Such side effects have been observed in drugs in a variety of drug classes including, for example, thyroid inhibitors, antibiotics, neuropsychotropics, cardiovascular medications, analgesics, antimalarials, nonsteroidal antiinflammatory agents, antihistamines and combinations thereof. See Lee, Wintrobe's Hematology, Lippincott, p. 1862–1869, and van der Klauw, M M et al., *Arch. Intern. Med.*, 1999, 159(4), p.369–374, the entire disclosures of which are incorporated herein.

Drugs that have been shown to cause neutropenia include, for example: trimethoprim, chloramphenicol, penicillins, cephalosporins, aminoglycosides, tetracyclines, nitroimidazoles, nitrofurantoin, flucytosine, rifampin, isoniazid, ethambutol, dapsone, sulfonamide antibiotics, clomiprimine, thiacetazone, dipyrone, sulfasalazine, mesalazine, ciprofloxacin, chloroquin, mebendazole, terbendafine, pyrimethamine, levamisole, ristocetin, griseofulvin, phenothiazines, benzodiazepines, amoxapine, meprobamate, barbiturates, clozapine, risperidone, imipramine, desipramine, thiothixene, haloperidol, valproic acid, hydantoins, succinimides, trimethadione, carbamazepine, procainamide, quinidine, propafenone, captopril, propranolol, hydralazine, methyldopa, ibuprofen, indomethacin, sulindac, tolmetin, aspirin, aminopyine, phenylbutazone, diflunisal, benoxaprofen, allopurinol, colchicine, propylthiouracil, thiouracil, methimazole, carbimazole, thiocyanate, potassium perchlorate, cimetidine, ranatadine, tripelennamine, methaphenilene, thenalidine, mianserin, bromopheneramine, quinine, hydroxychloroquin, quinacrine, diazoxide, dihydropyridines, ticlopidine, vesnarinone, aprindine, imipenem/cilastatin, zidovudine, fludarabine, acyclovir, turbinafine, aminoglutethimide, famotidine, bezafibrate, flutamide, tamoxafen, penicillamine, retinoic acid, metoclopramide, phenindone, dinitrophenol, ethacrynic acid, rauwolfia, ethanol, chlorpropamide, tolbutamide, thiazides, spironolactone, methazolamide, acetazolamide, levodopa and combinations thereof. See, Oyesanme et al., *Psychosomatics*, 40:5, September–October, 1999, p.414–421; the entire disclosure of which is incorporated herein by reference. Neutropenia induced by any of the aforementioned drugs may be treated or prevented according to the present invention.

A more common source of drug-induced neutropenia involves the severe neutropenia that predictably occurs after large doses of cytoreductive cancer drugs and which also accompanies ionizing radiation therapy. The predictability of neutropenia in an individual undergoing chemotherapy for cancer provides a basis for methods of the present invention for provide prophylactic administration. See The Merck Manual, 17$^{th}$ Ed., 1999 Chapter 135, "Leukopenia", the entire disclosure of which is incorporated herein by reference.

Instances wherein neutropenia may be prevented include administration to individuals receiving cancer chemotherapy or to individuals in preparation for imminent cancer chemotherapy. Methods of the invention also include administration to an individual in association with, or in preparation for other events that have been shown to increase the risk of the individual subsequently developing neutropenia. Such factors include, but are not limited to: Therapeutic radiation therapy; drug therapies other than cancer chemotherapy wherein the individual is known or suspected to have a sensitivity to the therapy that increases the risk of developing neutropenia; drug therapies other than cancer chemotherapy wherein the drug is associated with a high incidence of neutropenia, an immunodeficiency such Acquired Immunodeficiency Syndrome (AIDS); or a virus known to cause immunodeficiency, such as for example Human Immunodeficiency Virus (HIV).

The (R)-2,3-benzodiazepines of formula I useful in the present invention may be prepared by one of several methods. These methods generally follow the synthetic strategies and procedures used in the synthesis of 2,3-benzodiazepines such as tofisopam and tofisopam analogs. See U.S. Pat. Nos. 3,736,315 and 4,423,044 (tofisopam syntheses) and Horvath et al., *Progress in Neurobiology* 60(2000) p.309–342 and references cited therein (preparation of tofisopam and analogs thereof), the entire disclosures of which are incorporated herein by reference. In the synthesis methods that follow, the products of the chemical syntheses are racemic (R)- and (S)-2,3-benzodiazepines. These racemic mixtures are subsequently separated using known methods of resolution to produce the (R)-2,3-benzodiazepines of formula I substantially free of the (S)-enantiomers. By an "(R)-2,3-benzodiazepine" is meant a 2,3-benzodiazepine that has an (R) absolute conformation by virtue of a substitution at the 5-position of the benzodiazepine ring to give a resolvable chiral carbon at the 5-position. By an "(R)-2,3-benzodiazepine substantially free of the (S)-enantiomer" or "an (R)-enantiomer of a compound of formula I substantially free of the corresponding (S)-enantiomer" is meant a compound that comprises 80% or more by weight of the desired (R)-enantiomer and likewise contains 20% or less of the (S)-enantiomer as a contaminant, by weight. Preferably, compounds used in methods of the present invention have a composition that is 85% by weight or greater of the (R)-enantiomer, and 15% by weight, or less, of the (S)-enantiomer. More preferably, compounds used in methods of the present invention have a composition that is 90% by weight or greater of the (R)-enantiomer and 10% by weight, or less, of the (S)-enantiomer. More preferably, compounds used in methods of the present invention have a composition that is 95% by weight or greater of the (R)-enantiomer and 5% by weight, or less, of the (S)-enantiomer. Most preferably, compounds used in methods of the present invention have a composition that is 99% by weight or greater of the (R)-enantiomer and 1% by weight, or less, of the (S)-enantiomer.

Racemic 2,3-benzodiazepines may be synthesized, as shown in Scheme 1, from the corresponding 2-benzopyrilium salt H by reaction with hydrazine hydrate, wherein X$^-$ is a counterion such as, for example perchlorate:

Scheme 1

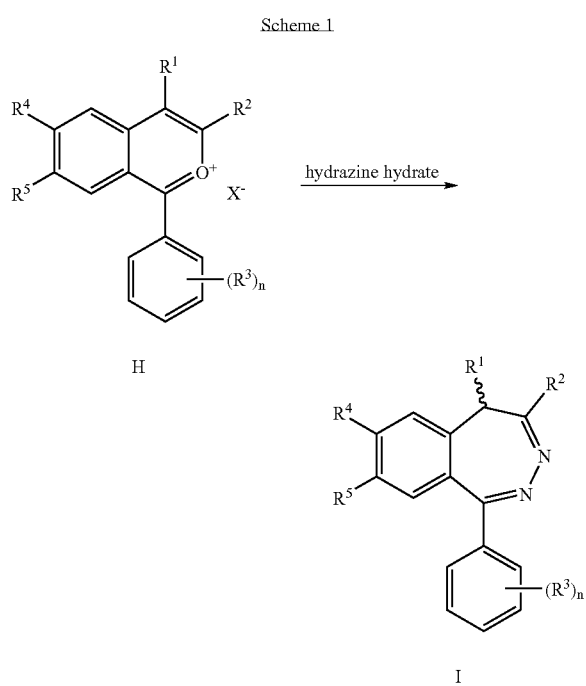

Accordingly, hydrazine hydrate (98%, approximately 3 equivalents based on the 2-benzopyrylium salt) is added dropwise to a stirred solution of the 2-benzopyrylium salt H in glacial acetic acid (approximately 1 mL/3 mmol of 2-benzopyrylium salt). During this operation, the solution is maintained at an elevated temperature, preferably, 80–100° C. The solution is then maintained a higher elevated temperature, preferably 95–100° C., for about one hour. Then the reaction mixture is diluted with 2% aqueous sodium hydroxide solution (approximately 3 equivalents based on the 2-benzopyrylium salt) and cooled. The product 2,3-benzodiazepine separates as a solid and is removed by filtration, washed with water and dried. The crude product may be purified by taking it up in a polar aprotic solvent such as dimethylformamide (DMF) at an elevated temperature, preferably 100–130° C., and decolorizing the solution with activated carbon. The carbon is removed by filtration and the filtered solution is diluted with water. The purified product precipitates out of the solution and is collected by filtration.

See Kórósi et al., U.S. Pat. No. 4,322,346, the entire disclosure of which is incorporated herein by reference, disclosing three variations of the reaction protocol for preparing a substituted 2,3-benzodiazepine from the precursor benzopyrilium salt.

Retrosynthetically, the intermediate benzopyrilium salt, H, may be prepared from one of several starting materials. According to one such method, illustrated in Scheme 2, intermediate H is prepared from the corresponding aryl ethanol derivative D via the isochroman intermediate F.

Another variation for preparing 2,3-benzodiazepines is illustrated in Scheme 3 and 4 (Examples 2 and 3). The synthesis there proceeds from intermediate G without isolation of the intermediate benzopyrilium salt H.

2-Benzopyrylium salts H may be synthesized from intermediate 2-substituted phenyl ethanol derivatives D through isochroman intermediate F, wherein X$^-$ is a counterion such as, for example, perchlorate:

Scheme 2

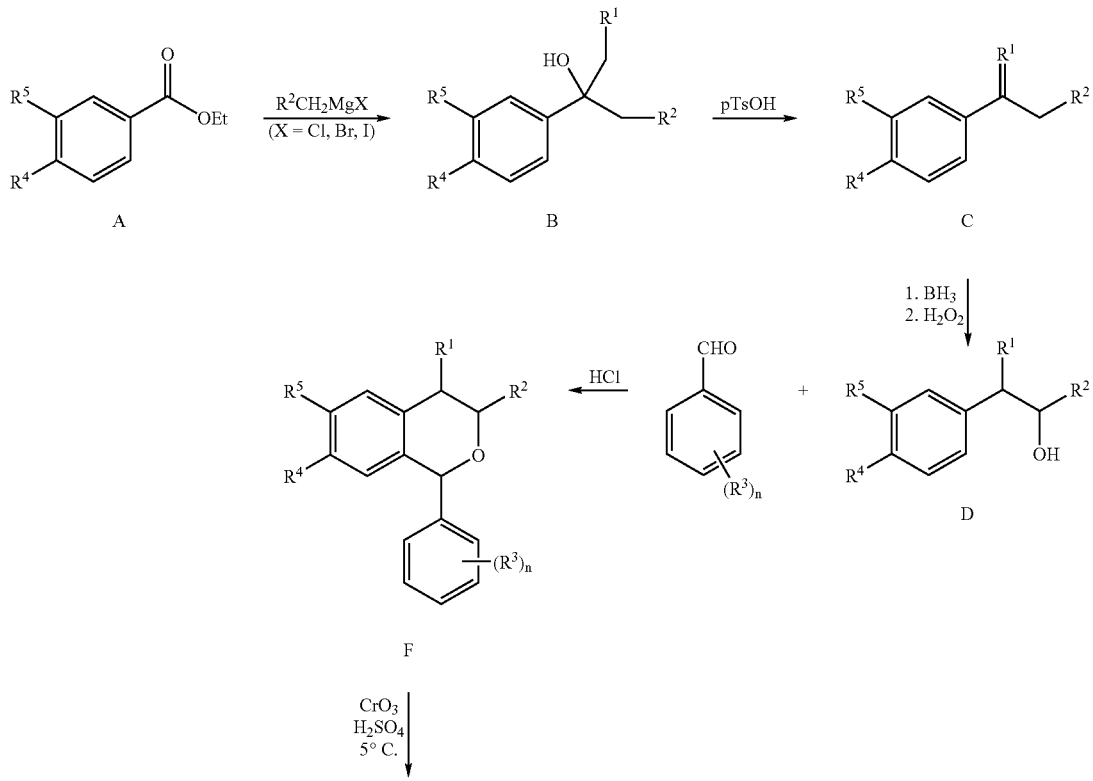

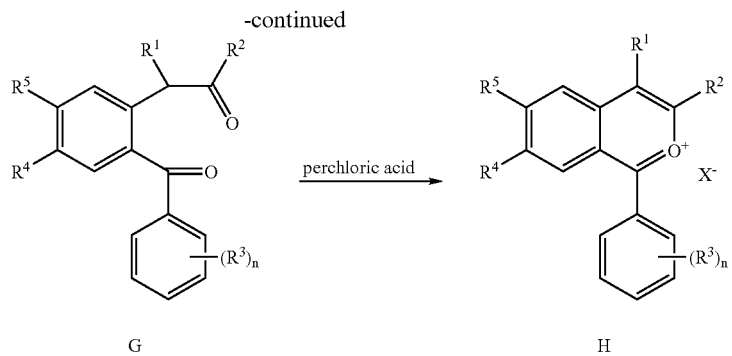

Accordingly, a substituted benzoic acid ester, A is dissolved in a suitable solvent, preferably ether and cooled to 0° C. Two equivalents of a suitable Grignard reagent are added dropwise and the reaction is allowed to warm to room temperature and monitored for disappearance of starting material. When the reaction is complete, it may be quenched with a proton source such as acetic acid. Volatiles are removed in vacuo, and the product B is used for the next step without purification.

The α,α-substituted benzyl alcohol B is taken up in a high boiling solvent such as toluene and a catalytic amount of para-toluene sulfonic acid (p-TsOH). The mixture is warmed to reflux and may be monitored for disappearance of starting materials. When the reaction is complete, the volatiles are removed in vacuo and the crude product C is purified by column chromatography.

The substituted styrene C is hydroxylated under anti-Markovnikov conditions to give intermediate phenylethyl alcohol D. A solution of D, and of a suitably substituted benzaldehyde E (1.2 eq) are added to anhydrous dioxane. The resulting solution is then saturated with gaseous HCl and warmed, preferably to reflux temperature for about one hour. The mixture is then cooled to room temperature, poured into water, basified (preferably with aqueous sodium hydroxide) and extracted with an organic solvent (preferably ethyl acetate). The extract is dried, filtered and concentrated under vacuum. The resulting residue is purified, preferably by crystallization, to yield F.

To a stirred, cooled, (preferably to 0–5° C.) solution of F (2 g) in acetone (30 mL), is added dropwise a solution of chromium trioxide (2 g) in 35% sulfuric acid (20 mL). The latter solution is added at a rate such that the reaction temperature remains below 5° C. After the addition is complete, the reaction mixture is allowed to rise to room temperature and is stirred at room temperature for two hours. The reaction mixture is then poured into water and extracted with an organic solvent, preferably ethyl acetate. The organic extract is washed with water and then with ice-cold 10% aqueous sodium hydroxide. The aqueous alkaline fraction is then acidified, preferably with dilute aqueous hydrochloric acid, and extracted with an organic solvent, preferably, chloroform. The chloroform extract is dried, filtered and concentrated under vacuum to give G. The crude residue may further be purified by column chromatography.

The 2-α-acyl hydrocarbylbenzophenone G (5 g) is dissolved in glacial acetic acid (15 mL). To this mixture is added 60% perchloric acid (7.5 mL). The resulting mixture is warmed to 100° C. (steam bath) for three minutes. The mixture is allowed to cool to room temperature. Crystallization of the crude product may begin spontaneously at this point or may be induced by addition of ether or ethyl acetate. The product 2-benzopyrylium salt H is removed by filtration and purified by recrystallization, preferably from ethanol or glacial acetic acid/ethyl acetate.

A similar synthetic sequence for preparation of 2,3-benzodiazepines is disclosed in U.S. Pat. No. 3,736,315, the entire disclosure of which is incorporated herein by reference. Synthetic strategies for preparation of 2,3-benzodiazepines are also disclosed in Horvath et al., *Progress in Neurobiology* 60(2000) p309–342 and references cited therein; the entire disclosures of which are incorporated herein by reference.

Alternative methods for preparation of intermediate H start with an aryl acetonide or indanone starting material. See Kunnetsov, E. V., and Dorofeenko, G. N., *Zh. Org. Khim.*, 6, 578–581. and M. Vajda, *Acta Chem. Acad. Sci. Hung*, 40, p.295–307, 1964, respectively, the entire disclosures of which are incorporated herein by reference.

To synthesize a 2,3-benzodiazepine derivative of formula I having an amine substituent, the starting aromatic amine components must be protected with a protecting group or otherwise rendered unreactive in order for the amine to be rendered stable to the reaction conditions employed in the reaction schemes shown or referenced above. A means of circumventing the need for a protecting group may be to use a starting material containing an aromatic nitro group(s) in place of the desired aromatic amino group(s). The nitro group performs the same function as an amine protecting group in this synthesis and it may, following the synthesis steps that are incompatible with an amine substituent, be then reduced to an amine. Reduction of the aromatic nitro group can be done, for example, via catalytic hydrogenation. Catalytic hydrogenation provides the capability to selectively reduce the aromatic nitro group without reducing the olefin or other functionality in the intermediate. This synthetic strategy is disclosed in U.S. Pat. No. 4,614,740, wherein racemic 2,3-benzodiazepines were prepared with amino groups at a position corresponding the $R^3$ of formula I of the present invention. The entire disclosure of U.S. Pat. No. 4,614,740 is incorporated herein by reference.

Resolution of (R)-2,3-Benzodiazepines of Formula I

The synthetic procedures shown (or referenced) above produce racemic mixtures of 2,3-benzodiazepines. In order to prepare (R)-2,3-benzodiazepines of formula I that are useful in methods of the present invention, the racemic mixture must be resolved.

Racemic 2,3-benzodiazepines may, for example, be converted to the (S)-dibenzoyltartaric acid salt, which is a diastereomeric mixture of SS and RS configurations. The pair of diastereomers (R,S) and (S,S) possess different properties, e.g., differential solubilities, that allow for the use of conventional separation methods. Fractional crystallization of diastereomeric salts from a suitable solvent is one such separation method. This resolution has been successfully applied to the resolution of racemic tofisopam. See Hungarian Patent 178516 and also Toth et al., *J. Heterocyclic Chem.*, 20:09–713 (1983), the entire disclosures of which are incorporated herein by reference.

Alternatively, racemic-2,3-benzodiazepines may be derivatized via, for example, acylation of an aryl hydroxy moiety, with a chiral acylating reagent, e.g., (S)-mandelic acid. The resulting ester, has a second chiral center, and thus exists as a diastereomeric pair separable using conventional methods such as crystallization or chromatography. Following the separation, the chiral moiety with which the racemic 2,3-benzodiazepine is derivatized, may be removed.

Racemic 2,3-benzodiazepines may be separated without diastereomer formation by differential absorption on a chiral stationary phase of a chromatography column, particularly a preparative HPLC column. Chiral HPLC columns are commercially available with a variety of packing materials to suit a broad range of separation applications. Exemplary stationary phases suitable for resolving the racemic 2,3-benzodiazepines include:

(i) macrocyclic glycopeptides, such as silica-bonded vancomycin which contains 18 chiral centers surrounding three pockets or cavities;

(ii) chiral $\alpha_1$-acid glycoprotein;

(iii) human serum albumin; and (iv) cellobiohydrolase (CBH).

Chiral $\alpha_1$-acid glycoprotein is a highly stable protein immobilized onto spherical silica particles that tolerates high concentrations of organic solvents, high and low pH, and high temperatures. Human serum albumin, though especially suited for the resolution of weak and strong acids, zwitterionic and nonprotolytic compounds, has been used to resolve basic compounds. CBH is a very stable enzyme which has been immobilized onto spherical silica particles and is preferentially used for the separation of enantiomers of basic drugs from many compound classes.

The resolution of tofisopam by chiral chromatography using macrocyclic glycopeptide as a stationary phase on a Chirobiotic V™ column (ASTEAC, Whippany, N.J.) is disclosed in U.S. Pat. No. 6,080,736. Fitos et al. (*J. Chromatogr.*, 709 265 (1995)), discloses another method for resolving racemic tofisopam by chiral chromatography using a chiral $\alpha_1$-acid glycoprotein as a stationary phase on a CHIRAL-AGP™ column (ChromTech, Cheshire, UK). The latter method separates the (R)- and (S)-enantiomers and also resolves the two conformers (discussed below) of each enantiomer. These chromatographic methods, may be used generally to separate racemic 2,3-benzodiazepines into individual (R)- and (S)-enantiomers. The Chirobiotic V™ column is available in a semi-preparative size as employed for the above separation 500 mm×10 mm). The stationary phase of the Chirobiotic V™ column is commercially available in bulk for packing of preparative chromatography columns with larger sample capacity.

(R)- and (S)-enantiomers of 2,3-benzodiazepines may also exist in two stable conformations that may be assumed by the benzodiazepine ring, as generally depicted below:

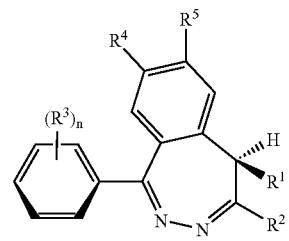

R(+)-isomer

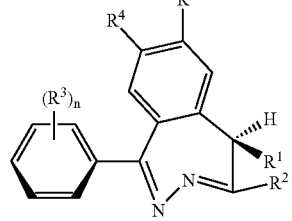

R(-)-isomer

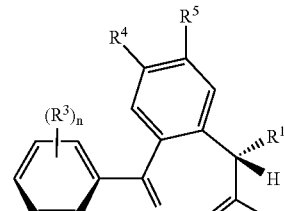

S(-)-isomer

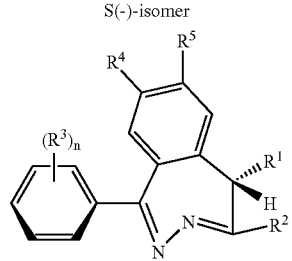

S(+)-isomer

The present invention includes methods as described herein that use any and all observable conformations of compounds of formula I (of the (R)- absolute configuration at carbon 5 of the benzodiazepine ring) which are biologically active in treatments to raise neutrophil levels.

Differential binding of the (+) and (−) conformers of 2,3-benzodiazepines generally, has been reported for tofisopam in binding studies with human albumin (Simongi et al. *Biochem. Pharm.*, 32(12), 1917–1920, 1983). The (+) and (−) conformers of tofisopam have also been reported as existing in an equilibrium (Zsila et al., *Journal of Liquid Chromatography & Related Technologies*, 22(5), 713–719, 1999; and references therein).

It will be understood that compounds of formula I useful in the methods of the present invention may contain one or more chiral centers in addition to chiral center at the 5-position of the benzodiazepine ring of compounds of formula I. Such compounds may exist in, and may be isolated as pure enantiomeric or diastereomeric forms or as racemic mixtures. The present invention includes methods that use any possible enantiomers, diastereomers, racemates or mixtures thereof of formula I (dictated by a chiral center other than the 5-position of the benzodiazepine ring) which are biologically active in treatments to raise neutrophil levels.

The compounds used in the methods of the present invention may take the form of pharmaceutically-acceptable salts. The term "salts", embraces salts commonly used to form alkali metal salts and to form addition salts of free acids or free bases. The term "pharmaceutically-acceptable salt" refers to salts that possess toxicity profiles within a range so as to have utility in pharmaceutical applications. Pharmaceutically unacceptable salts may nonetheless possess properties such as high crystallinity, which have utility in the practice of the present invention, such as for example utility in a synthetic process or in the resolution of enantiomers. Suitable acid addition salts may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, example of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, salicyclic, salicyclic, 4-hydroxybenzoic, phenylacetic, mandelic, embonic (pamoic), methanesulfonic, ethanesulfonic, benzenesulfonic, pantothenic, 2-hydroxyethanesulfonic, toluenesulfonic, sulfanilic, cyclohexylaminosulfonic, stearic, algenic, beta-hydroxybutyric, salicyclic, galactaric and galacturonic acid.

Suitable base addition salts of compounds of formula I useful in methods of the invention include for example, metallic salts made from calcium, magnesium, potassium, sodium and zinc or organic salts made from N,N'-dibenzylethylenediamine, chloroprocaine, choline, diethanolamine, ethylenediamine, meglumine (N-methylglucamine) and procaine. All of these salts may be prepared by conventional means from the corresponding compound of formula I by reacting, for example, the appropriate acid or base with the compound of formula I.

The compounds useful in methods of the invention may be administered to individuals (mammals, including animals and humans) for treatment or prevention of neutropenia.

For treating or preventing neutropenia, the specific dose of compound according to the invention to obtain therapeutic benefit will, of. course, be determined by the particular circumstances of the individual patient including, the size, weight, age and sex of the patient. Also determinative will be the nature and stage of the disease and the route of administration. For example, a daily dosage of from about 100 to 1500 mg/day may be utilized. Preferably, a daily dosage of from about 100 to 1000 mg/day may be utilized. More preferably, a daily dosage of from about 100 to 500 mg/day may be utilized. Higher or lower doses are also contemplated. Neutrophil levels may be monitored in the patient and the treatment regimen may be maintained until neutrophil levels reach a normal range.

For prophylactic administration, the compounds useful in the practice of methods of the invention should be administered far enough in advance of a known event that increases the risk of neutropenia such that the compound is able to reach the site of action in sufficient concentration to exert therapeutic effect. The pharmacokinetics of specific compounds may be determined by means known in the art and tissue levels of a compound in a particular individual may be determined by conventional analyses.

One or more compounds useful in the practice of the present inventions may be administered simultaneously, or different (R)-2,3-benzodiazepines useful in the practice of the present invention may be administered at different times during treatment or prevention therapy.

The methods of the present invention may comprise administering (R)-2,3-benzodiazepines in the form of a pharmaceutical composition, in combination with a pharmaceutically acceptable carrier. The active ingredient in such formulations may comprise from 0.1 to 99.99 weight percent. By "pharmaceutically acceptable carrier" is meant any carrier, diluent or excipient that is compatible with the other ingredients of the formulation and to deleterious to the recipient.

The compounds useful in methods of the invention may be administered for therapeutic effect by any route, for example enteral (e.g., oral, rectal, intranasal, etc.) and parenteral administration. Parenteral administration includes, for example, intravenous, intramuscular, intraarterial, intraperitoneal, intravaginal, intravesical (e.g., into the bladder), intradermal, topical or subcutaneous administration. Also contemplated within the scope of the invention is the instillation of drug in the body of the patient in a controlled formulation, with systemic or local release of the drug to occur at a later time. For use to increase neutrophil levels, the drug may be localized in a depot for controlled release to the circulation.

The active agent is preferably administered with a pharmaceutically acceptable carrier selected on the basis of the selected route of administration and standard pharmaceutical practice. The active agent may be formulated into dosage forms according to standard practices in the field of pharmaceutical preparations. See Alphonso Gennaro, ed., *Remington's Pharmaceutical Sciences,* 18th Ed., (1990) Mack Publishing Co., Easton, Pa. Suitable dosage forms may comprise, for example, tablets, capsules, solutions, parenteral solutions, troches, suppositories, or suspensions.

For parenteral administration, the active agent may be mixed with a suitable carrier or diluent such as water, an oil (particularly a vegetable oil), ethanol, saline solution, aqueous dextrose (glucose) and related sugar solutions, glycerol, or a glycol such as propylene glycol or polyethylene glycol. Solutions for parenteral administration preferably contain a pharmaceutically-acceptable water-soluble salt of the active agent. Stabilizing agents, antioxidizing agents and preservatives may also be added. Suitable antioxidizing agents include sulfite, ascorbic acid, citric acid and its salts, and sodium EDTA. Suitable preservatives include benzalkonium chloride, methyl- or propyl-paraben, and chlorbutanol. The composition for parenteral administration may take the form of an aqueous or nonaqueous solution, dispersion, suspension or emulsion.

For oral administration, the active agent may be combined with one or more solid inactive ingredients for the preparation of tablets, capsules, pills, powders, granules or other suitable oral dosage forms. For example, the active agent may be combined with at least one excipient such as fillers, binders, humectants, disintegrating agents, solution retarders, absorption accelerators, wetting agents absorbents or lubricating agents. According to one tablet embodiment, the active agent may be combined with carboxymethylcellulose calcium, magnesium stearate, mannitol and starch, and then formed into tablets by conventional tableting methods.

The compositions of the present invention can also be formulated so as to provide slow or controlled-release of the active ingredient therein. In general, a controlled-release preparation is a composition capable of releasing the active ingredient at the required rate to maintain constant pharmacological activity for a desirable period of time. Such dosage forms can provide a supply of a drug to the body during a predetermined period of time and thus maintain drug levels in the therapeutic range for longer periods of time than other non-controlled formulations.

For example, U.S. Pat. No. 5,674,533 discloses controlled-release compositions in liquid dosage forms for the administration of moguisteine, a potent peripheral antitussive. U.S. Pat. No. 5,059,595 describes the controlled-release of active agents by the use of a gastro-resistant tablet for the therapy of organic mental disturbances. U.S. Pat. No. 5,591,767 discloses a liquid reservoir transdermal patch for the controlled administration of ketorolac, a non-steroidal anti-inflammatory agent with potent analgesic properties. U.S. Pat. No. 5,120,548 discloses a controlled-release drug delivery device comprised of swellable polymers. U.S. Pat. No. 5,073,543 discloses controlled-release formulations containing a trophic factor entrapped by a ganglioside-liposome vehicle. U.S. Pat. No. 5,639,476 discloses a stable solid controlled-release formulation having a coating derived from an aqueous dispersion of a hydrophobic acrylic polymer. The patents cited above are incorporated herein by reference.

Biodegradable microparticles can be used in the controlled-release formulations of this invention. For example, U.S. Pat. No. 5,354,566 discloses a controlled-release powder that contains the active ingredient. U.S. Pat. No. 5,733,566 describes the use of polymeric microparticles that release antiparasitic compositions. These patents are incorporated herein by reference.

The controlled-release of the active ingredient can be stimulated by various inducers, for example pH, temperature, enzymes, water, or other physiological conditions or compounds. Various mechanisms of drug release exist. For example, in one embodiment, the controlled-release component can swell and form porous openings large enough to release the active ingredient after administration to a patient. The term "controlled-release component" in the context of the present invention is defined herein as a compound or compounds, such as polymers, polymer matrices, gels, permeable membranes, liposomes and/or microspheres, that facilitate the controlled-release of the active ingredient (e.g., (R)-tofisopam or a pharmaceutically-acceptable salt thereof) in the pharmaceutical composition. In another embodiment, the controlled-release component is biodegradable, induced by exposure to the aqueous environment; pH, temperature, or enzymes in the body. In another embodiment, sol-gels can be used, wherein the active ingredient is incorporated into a sol-gel matrix that is a solid at room temperature. This matrix is implanted into a patient, preferably a mammal, having a body temperature high enough to induce gel formation of the sol-gel matrix, thereby releasing the active ingredient into the patient.

The practice of the invention is illustrated by the following non-limiting examples.

EXAMPLES

Example 1

Synthesis of (R)-1-(3,4-dimethoxyphenyl)-4-methyl-5-ethyl-7-hydroxy-8-methoxy-5H-2,3-benzodiazepine A. Synthesis of Racemic 1-(3,4-dimethoxyphenyl)-4-methyl-5-ethyl-7-hydroxy-8-methoxy-5H-2,3-benzodiazepine:

4.41 g (10 mmol) of 1-(3,4-dimethoxyphenyl)-3-methyl-4-ethyl-6,7-dimethoxyisobenzopyrilium chloride hydrochloride is dissolved in methanol (35 mL) at a temperature of 40° C. After cooling to 20–25° C., hydrazine hydrate (0.75 g, 15 mmol, dissolved in 5 mL methanol) is added. The reaction is monitored by HPLC and when complete, is evaporated to dryness. The residue is triturated with cold water (3 mL), filtered and dried to yield the crude (R,S)-1-(33,4-dimethoxyphenyl)-4-methyl-5-ethyl-7-hydroxy-8-methoxy-5H-2,3-benzodiazepine which is subsequently triturated with hot ethyl acetate to yield the pure product.

B. Resolution of the Racemate to Produce (R)-1-(3,4-dimethoxyphenyl)-4-methyl-5-ethyl-7-hydroxy-8-methoxy-5H-2,3-benzodiazepine:

(R,S)-1-(3,4-Dimethoxyphenyl)-4-methyl-5-ethyl-7-hydroxy-8-methoxy-5H-2,3-benzodiazepine (43 mg, dissolved in acetonitrile) is injected onto a Chirobiotic V column (ASTEAC, Whippany, N.J.) Elution of the racemate with methyl-tert-butyl ether/acetonitrile 90/10 (v/v), at 40 mL/minute, is monitored at 310 nm, 2 mm path.

The R(+) enantiomer is the first compound to elute, and is collected and dried. The R(−), S(+), S(−) enantiomers, and some residual R(+) enantiomer coelute and are collected in subsequent fractions. Approximately 20% of the R(+) isomer is converted to the R(−) isomer if left in the eluent for 24 hours. A stable 80/20 equilibrium (R(+) to R(−)) is observed between the conformers in the eluent solution.

Example 2

Synthesis of racemic-1-(3-hydroxy-4-methoxyphenyl)-4-methyl-5-ethyl-7,8-dimethoxy-5H-2,3-benzodiazepine Racemic-1-(3-hydroxy-4-methoxyphenyl)-4-methyl-5-ethyl-7,8-dimethoxy-5H-2,3-benzodiazepine was synthesized according to the route of Scheme 3.

Scheme 3

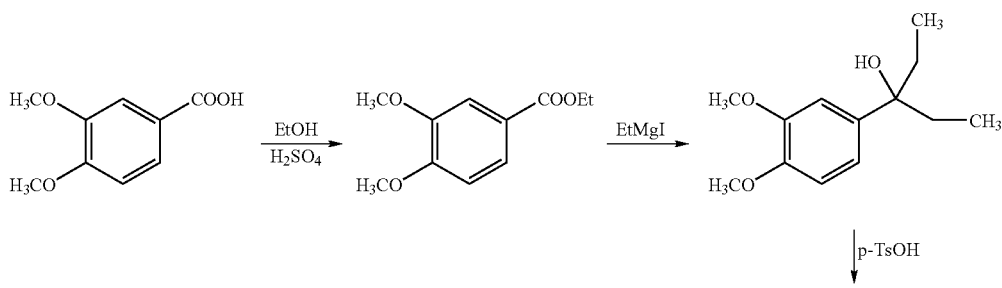

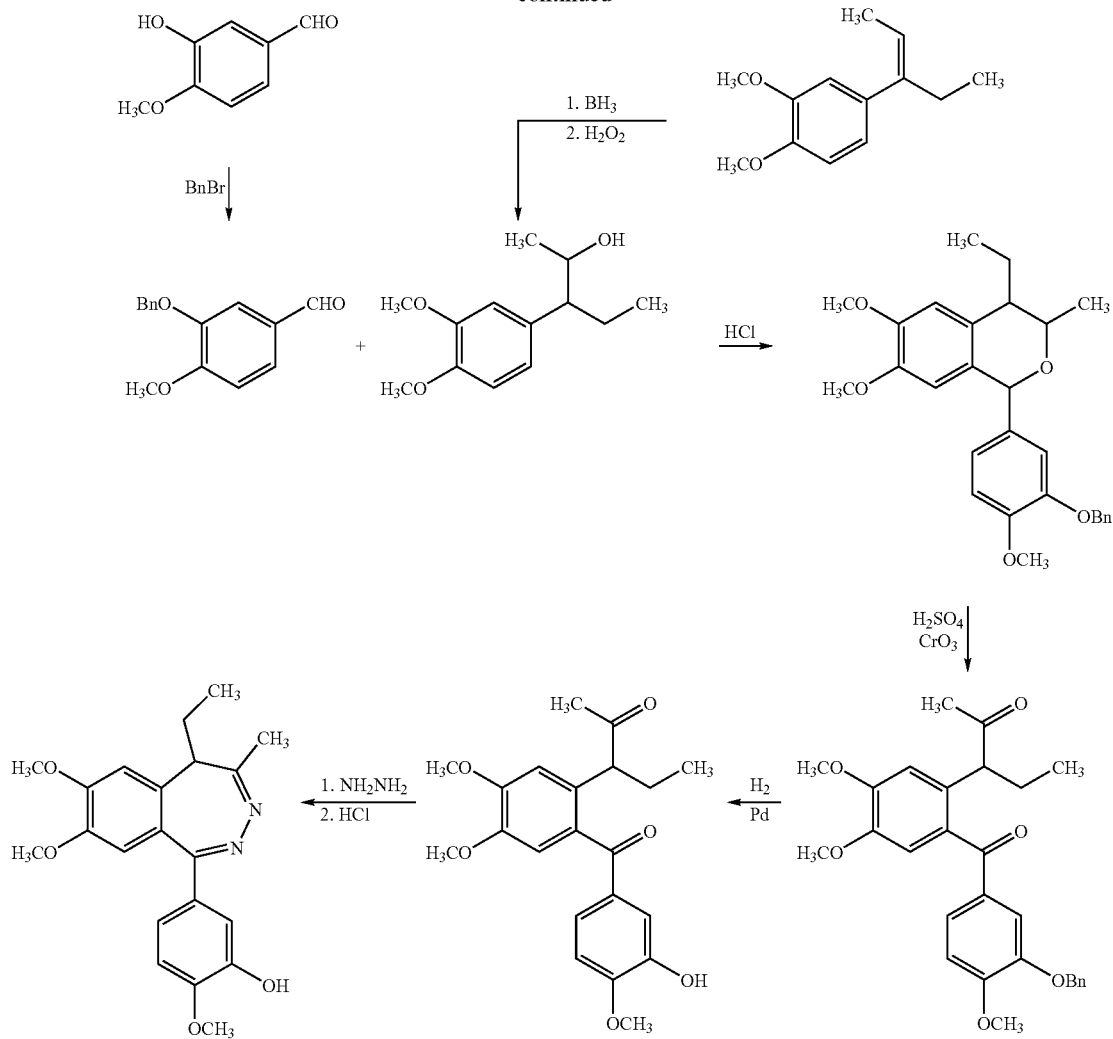

A. Esterification of 3,4-dimethoxybenzoic Acid to Yield ethyl-3,4-dimethoxybenzoate([3943-77-9]).

A solution of 200 g of 3,4-dimethoxybenzoic acid and 35 g of concentrated sulfuric acid in 600 mL of absolute ethanol was heated at reflux overnight. The mixture was concentrated and the residue poured into water. Methylene chloride was added and the solution washed successively with water, dilute sodium bicarbonate and water, then dried and concentrated. The residue was recrystallized from acetone/hexane.

B. Addition of Ethyl Magnesium Iodide to ethyl-3,4-dimethoxybenzoate Acid to yield 3-(3,4-dimethoxyphenyl)pentan-3-ol.

A solution of 4.8 mL of iodoethane in 20 mL of ether was added dropwise to a suspension of 1.5 g of magnesium turnings in 10 mL of ether. After 5 mL of the iodoethane solution had been added, a few grains of iodine were added and the mixture was heated to induce formation of the Grignard reagent. The remaining iodoethane solution was then added. After the Grignard formation was complete, a solution of 5 g of ethyl 3,4-dimethoxybenzoate in ether was added and the mixture was allowed to stir at room temperature overnight. The reaction was quenched by addition of saturated ammonium chloride. The mixture was extracted with ether. The combined ether extracts were dried and concentrated to an oily residue. Yield: 5 g.

C. Elimination of $H_2O$ From 3-(3,4-dimethoxyphenyl)pentan-3-ol to yield 4-((1Z)-1-ethylprop-1-enyl)-1,2-dimethoxybenzene.

A solution of 5 g of crude 3-(3,4-dimethoxyphenyl)pentan-3-ol and 0.25 g of p-tolenesulfonic acid in 80 mL of benzene was heated at reflux for 1 hr with azeotropic removal of water. The mixture was then filtered through a pad of sodium bicarbonate and the filtrate concentrated. The residue was purified by distillation under reduced pressure. Yield: 2.9 g.

D. Addition of $H_2O$ to 4-((1Z)-1-ethylprop-1-enyl)-1,2-dimethoxybenzene to yield 3-(3,4-dimethoxyphenyl)pentan-2-ol.

To a solution of 26 g of 4-((1Z)-1-ethylprop-1-enyl)-1,2-dimethoxybenzene in tetrahydrofuran at 0° C. was added 189 mL of a 1.0M solution of borane-tetrahydrofuran complex in tetrahydrofuran. The mixture was stirred for 3 hr at 0° C., then 35.6 mL of 50% hydrogen peroxide was added, with simultaneous addition of 5M sodium hydroxide to maintain the mixture at pH 8. The mixture was extracted with ether. The combined ether extracts were dried and concentrated.

E. Benzylation of 3-hydroxy-4-methoxybenzaldehyde to yield 4-methoxy-3-(phenylmethoxy)benzaldehyde ([6346-05-0]).

A solution of 100 g of 3-hydroxy-4-methoxybenzaldehyde and 135 g of benzyl bromide in 500 mL of acetone containing a suspension of 137 g of potassium carbonate was heated at reflux overnight. The mixture was filtered, the filtrate concentrated and the residue recrystallized from toluene/hexane. Yield: 65 g.

F. Reaction of 3-(3,4-dimethoxyphenyl)pentan-2-ol with 4-methoxy-3-(phenylmethoxy)benzaldehyde to yield 4-(4-ethyl-6,7-dimethoxy-3-methylisochromanyl)-1-methoxy-2-(phenylmethoxy)benzene.

A solution of 14 g of 4-methoxy-3-(phenylmethoxy) benzaldehyde and 15 g of 3-(3,4-dimethoxyphenyl)pentan-2-ol in 0.3 L of dioxane was saturated with hydrogen chloride gas. The mixture was heated at reflux for 3 hr, saturated again with hydrogen chloride gas and allowed to stir at room temperature overnight. It was then poured into water, basified with dilute sodium hydroxide and extracted with methylene chloride. The combined methylene chloride extracts were dried and concentrated.

G. Ring-Opening of 4-(4-ethyl-6,7-dimethoxy-3-methylisochromanyl)-1-methoxy-2-(phenylmethoxy)benzene to Yield 3-(4,5-dimethoxy-2-{[4-methoxy-3-(phenylmethoxy)phenyl]carbonyl}phenyl)pentan-2-one.

To a solution of 30 g of crude 4-(4-ethyl-6,7-dimethoxy-3-methylisochromanyl)-1-methoxy-2-(phenylmethoxy)benzene in 450 mL of acetone at 5° C. was added a solution of 30 g of chromic oxide in 300 mL of 35% sulfuric acid. The mixture was stirred at room temperature for 2 hr, neutralized by adding cold 10% sodium hydroxide and concentrated to remove acetone. Then, water was added and the mixture was extracted with methylene chloride. The combined methylene chloride extracts were dried and concentrated. The residue was purified by column chromatography on silica gel. Yield: 10 g H. Debenzylation of 3-(4,5-dimethoxy-2-{[4-methoxy-3-(phenylmethoxy)-phenyl]carbonyl}phenyl)pentan-2-one to yield 3-{2-[(3-hydroxy-4-methoxyphenyl)carbonyl]-4,5-dimethoxyphenyl}pentan-2-one.

A solution of 10 g of 3-(4,5-dimethoxy-2-{[4-methoxy-3-(phenylmethoxy)-phenyl]carbonyl}phenyl)pentan-2-one in methylene chloride containing a suspension of 0.9 g of 10% palladium on carbon was hydrogenated at 80 psi for 1 hr. The mixture was filtered through diatomaceous earth and the filtrate concentrated. Yield: 6.5 g I. Annulation of 3-{2-[(3-hydroxy-4-methoxyphenyl)carbonyl]-4,5-dimethoxyphenyl}pentan-2-one by Reaction with Hydrazine to yield 1-(3-hydroxy-4-methoxyphenyl)-4-methyl-5-ethyl-7,8-dimethoxy-5H-2,3-benzodiazepine.

A solution of 6.5 g of 3-{2-[(3-hydroxy-4-methoxyphenyl)carbonyl]-4,5-dimethoxyphenyl}pentan-2-one and 2.2 mL of hydrazine in 130 mL of ethanol was heated at reflux for 0.5 hr. After allowing the solution to cool to room temperature, it was saturated with HCl gas. The mixture was then concentrated to a volume of about 5 mL, basified with concentrated ammonium hydroxide, and extracted with methylene chloride. The combined methylene chloride extracts were dried and concentrated, and the residue recrystallized from ethyl acetate/hexane. Yield: 0.97 g The product 1-(3-hydroxy-4-methoxyphenyl)-4-methyl-5-ethyl-7,8-dimethoxy-5H-2,3-benzodiazepine was analyzed by HPLC, elemental analysis, GC/MS, proton NMR and differential scanning calorimetry (DSC). The data are as follows:

Purity: 99.29% by HPLC (% area). Column: Betasil Phenyl 4.6×150 mm. Mobile Phase: Acetonitrile::0.01M Phosphate Buffer (70::30). Flow Rate: 0.5 mL/min. Wavelength: 254 nm.

GC-MS; M/e=358; with the fragmentation pattern matching the proposed structure.

DSC: Temperature program 100° C. to 300° C. at 5° C./min, indicated molar purity=99.75% and melting point of 158.6° C.

Elemental analysis (calculated/analysis): % C—68.09/68.08; % H—6.61/6.57; N—7.53/7.35. Calculated values include 0.02 equivalents of ethyl acetate and 0.09 equivalents of residual water.

NMR (DCCl$_3$) (performed on GE QE 300): 1.08 ppm (t, 3H); 1.99 (s, 3H); 2.11 (m, 2H); 2.75 (m, 1H); 3.75 (s, 3H); 3.93 (s, 3H); 3.97 (s, 3H); 6.46 (bs, 1H); 6.72 (s, 1H); 6.86 (m, 2H); 7.18 (d, 1H); 7.48 (s, 1H).

Example 3

Synthesis of 1-(3,4-dimethoxyphenyl)-4-methyl-5-ethyl-7 methoxy-8-hydroxy-5H-2,3-benzodiazepine Racemic 1-(3,4-dimethoxyphenyl)-4-methyl-5-ethyl-7-methoxy-8-hydroxy-5H-2,3-benzodiazepine was synthesized according to the route of Scheme 4.

Scheme 4

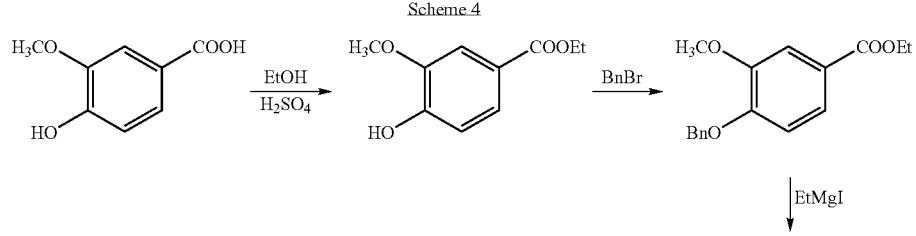

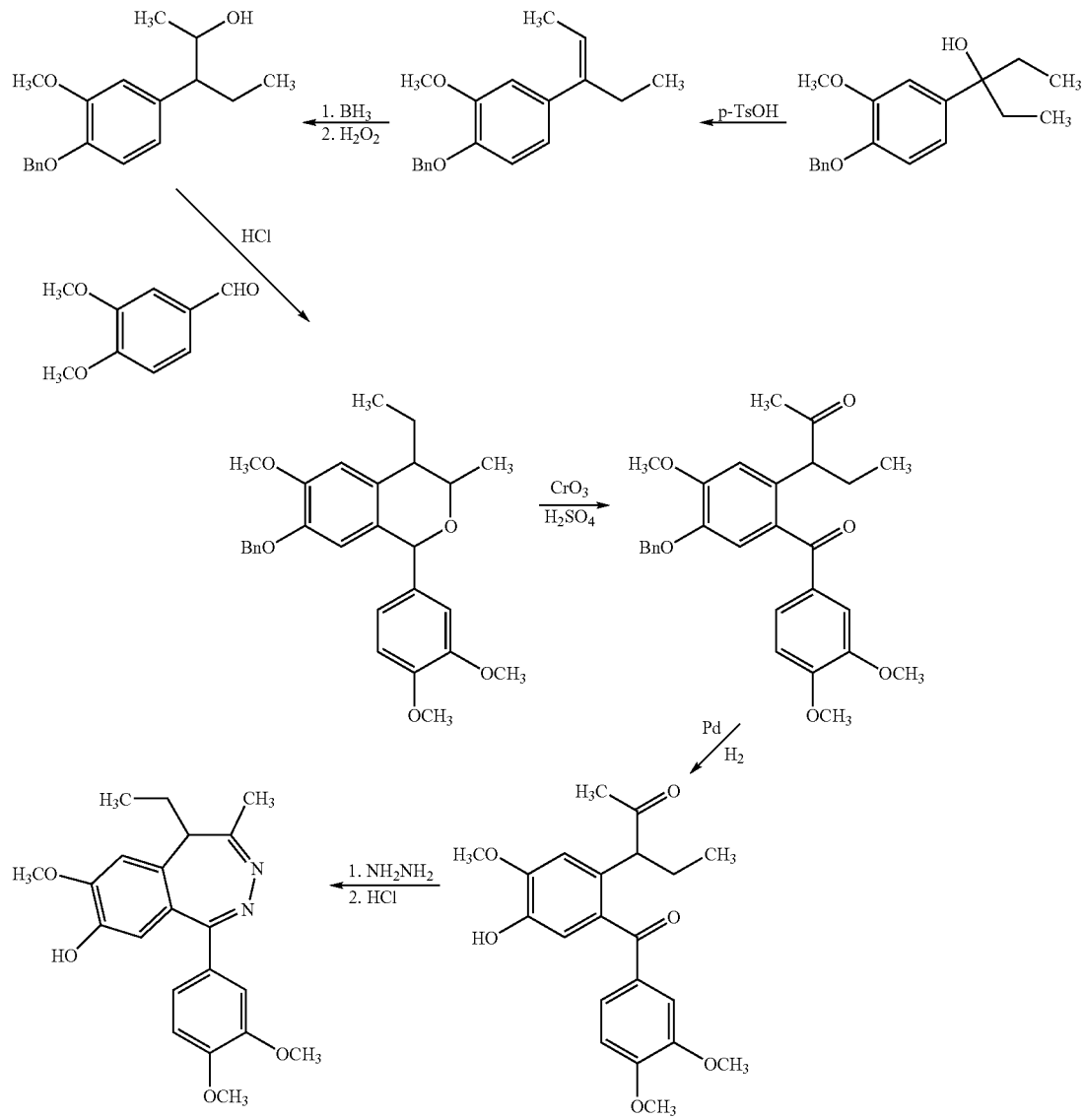

-continued

A. Esterification of 3-methoxy-4-hydroxybenzoic Acid to yield ethyl-3-methoxy-4-hydroxybenzoate.

A solution of 100 g of 3-methoxy-4-hydroxybenzoic acid and 17 g of concentrated sulfuric acid in 300 mL of absolute ethanol was heated at reflux overnight. The mixture was concentrated and the residue poured into water. Methylene chloride was added and the solution washed successively with water, dilute sodium bicarbonate and water, then dried and concentrated. Yield: 118 g B. Benzylation of ethyl-3-methoxy-4-hydroxybenzoate to yield ethyl-3-methoxy-4-benzyloxybenzoate.

A solution of 118 g of ethyl-3-methoxy-4-hydroxybenzoate and 86 mL of benzyl bromide in 600 mL of acetone containing a suspension of 124 g of potassium carbonate was heated at reflux overnight. The mixture was filtered, the filtrate concentrated and the residue recrystallized from acetone.

C. Addition of Ethyl Magnesium Iodide to ethyl-3-methoxy-4-benzyloxybenzoate to Yield 3-(3-methoxy-4-benzyloxyphenyl)pentan-3-ol.

Iodoethane (112 mL) was added dropwise to a suspension of 35 g of magnesium turnings in 160 mL of ether. After the formation of ethyl magnesium iodide was complete, a solution of 142 g of ethyl 3-methoxy-4-benzyloxybenzoate in ether was added and the mixture was allowed to stir at room temperature for 3 days. The reaction was quenched by addition of saturated ammonium chloride. The layers were separated and the ether layer was dried and concentrated to an oily residue. yield: 110 g.

D. Elimination of $H_2O$ from 3-(3-methoxy-4-benzyloxyphenyl)pentan-3-ol to yield 4-((1Z)-1-ethylprop-1-enyl)-1-benzyloxy-2-methoxybenzene.

A solution of 110 g of crude 3-(3-methoxy-4-benzyloxyphenyl)pentan-3-ol and 7 g of p-tolenesulfonic acid in 2 L of benzene was heated at reflux for 4 hr with azeotropic removal of water. The mixture was then filtered through a pad of sodium bicarbonate and the filtrate concentrated. The residue was purified by column chromatography on neutral alumina.

E. Addition of $H_2O$ to 4-((1Z)-1-ethylprop-1-enyl)-1-benzyloxy-2-methoxybenzene to yield 3-(3-methoxy-4-benzyloxyphenyl)pentan-2-ol.

To a solution of 96 g of 4-((1Z)-1-ethylprop-1-enyl)-1-benzyloxy-2-methoxybenzene in tetrahydrofuran at 0° C. was added 510 mL of a 1.0M solution of borane-tetrahydrofuran complex in tetrahydrofuran. The mixture was stirred for 3 hr at 0° C., then 204 mL of 25% hydrogen peroxide was added. The mixture was adjusted to pH 8 by addition of SM sodium hydroxide and extracted with ether. The combined ether extracts were dried and concentrated. Yield: 102 g.

F. Reaction of 3-(3-methoxy-4-benzyloxyphenyl)pentan-2-ol with 3,4-dimethoxybenzaldehyde to Yield 4-(4-ethyl-6-methoxy-7-benzyloxy-3-methyliso-chromanyl)-1,2-dimethoxybenzene.

A solution of 46 g of 3,4-dimethoxybenzaldehyde and 100 g of crude 3-(3-methoxy-4-benzyloxyphenyl)pentan-2-ol in 0.3 L of dioxane was saturated with hydrogen chloride gas. The mixture was heated at reflux for 3 hr, then poured into water, basified with dilute sodium hydroxide and extracted with methylene chloride. The combined methylene chloride extracts were dried and concentrated.

G. Ring-Opening of 4-(4-ethyl-6-methoxy-7-benzyloxy-3-methylisochromanyl)-1,2-dimethoxybenzene to Yield 3-(4-benzyloxy-5-methoxy-2-{[3,4-dimethoxyphenyl]carbonyl}phenyl)pentan-2-one.

To a solution of 50 g of crude 4-(4-ethyl-6-methoxy-7-benzyloxy-3-methyliso-chromanyl)-1,2-dimethoxybenzene in acetone at 5° C. was added a solution of 50 g of chromic oxide in 500 mL of 35% sulfuric acid. The mixture was stirred at room temperature for 2 hr, neutralized by adding cold 10% sodium hydroxide and concentrated to remove acetone. Water was added and the mixture extracted with methylene chloride. The combined methylene chloride extracts were dried and concentrated. The residue was purified by column chromatography on silica gel. Yield: 18 g H. Debenzylation of 3-(4-benzyloxy-5-methoxy-2-{[3,4-dimethoxyphenyl]carbonyl}phenyl)pentan-2-one to yield 3-{2-[(3,4-dimethoxyphenyl)carbonyl]-4-hydroxy-5-methoxyphenyl}pentan-2-one.

A solution of 18 g of 3-(4-benzyloxy-5-methoxy-2-{[3, 4-dimethoxyphenyl]carbonyl}phenyl)pentan-2-one in methylene chloride containing a suspension of 2 g of 10% palladium on carbon was hydrogenated at 80 psi for 1 hr. The mixture was filtered through diatomaceous earth and the filtrate concentrated. Yield: 15 g I. Annulation of 3-{2-[(3,4-dimethoxyphenyl)carbonyl]-4-hydroxy-5-methoxyphenyl}pentan-2-one by Reaction with Hydrazine to yield 1-(3,4-dimethoxyphenyl)-4-methyl-5-ethyl-7-methoxy-8-hydroxy-5H-2,3-benzodiazepine.

A solution of 14 g of 3-{2-[(3,4-dimethoxyphenyl)carbonyl]-4-hydroxy-5-methoxyphenyl}pentan-2-one and 4.7 mL of hydrazine in 280 mL of ethanol was heated at reflux for 0.5 hr. After allowing the solution to cool to room temperature, it was saturated with HCl gas. The mixture was then concentrated to a volume of about 5 mL, basified with concentrated ammonium hydroxide, and extracted with methylene chloride. The combined methylene chloride extracts were dried and concentrated, and the residue recrystallized from ethyl acetate/hexane. Yield: 1.5 g The product 1-(3,4-dimethoxyphenyl)-4-methyl-5-ethyl-7-methoxy-8-hydroxy-5H-2,3-benzodiazepine was analyzed by HPLC, elemental analysis, GC/MS, proton NMR and differential scanning calorimetry (DSC). The data are as follows:

Purity: 98.36% by HPLC (% area). Column: Betasil Phenyl 4.6×150 mm. Mobile Phase: Acetonitrile::0.01M Phosphate Buffer (70::30). Flow Rate: 0.5 mL/min. Wavelength: 254 nm.

GC-MS; M/e=358; with the fragmentation pattern matching the proposed structure.

Differential scanning calorimetry (DSC): Temperature program 100° C. to 300° C. at 5° C./min, indicated molar purity=99.14% and melting point of 146.2° C.

Elemental analysis (calculated/analysis): % C—68.14/68.12; % H—6.63/6.63; N—7.43/7.20. The calculated values include 0.1M of residual ethyl acetate.

NMR ($DCCl_3$) (performed on GE QE 300): 1.08 ppm (t, 3H); 1.96 (s, 3H); 2.10 (m, 2H); 2.77 (m, 1H); 3.91 (s, 3H); 3.93 (s, 3H); 3.98 (s, 3H); 5.73 (bs, 1H); 6.70 (s, 1H); 6.80 (d, 1H); 6.95 (s, 1H); 7.00 (d, 1H); 7.58 (s, 1H).

Example 4

Resolution of 1-(3-hydroxy-4-methoxyphenyl)-4-methyl-5-ethyl-7,8-dimethoxy-5H-2.3-benzodiazepine The enantiomers of racemic-1-(3-hydroxy-4-methoxyphenyl)-4-methyl-5-ethyl-7,8-dimethoxy-5H-2,3-benzodiazepine are resolved by chiral chromatography as follows.

Racemic-1-(3-hydroxy-4-methoxyphenyl)-4-methyl-5-ethyl-7,8-dimethoxy-5H-2,3-benzodiazepine is loaded onto a semipreparative (500 mm×10 mm) Chirobiotic V column (ASTEC, Whippany, N.J.) Eluton of the enantiomeric mixture with methyl-tert-butyl ether/acetonitrile (90/10 V/V), at a flow rate of 40 mL/min, is monitored at 310 nm. Fraction size is 10–20 mL and fractions are subjected to analytical chromatography using the same solvent composition on an analytical (150×4.6 mm) Chirobiotic V column. The fractions containing each isolated enantiomer are processed by removing the elution solvent in vacuo.

Example 5

Increase in Neutrophil Production in 16-Day Study in Rat.

The present assay was performed as follows: Eighty test animals; Crl:CD® (SD)IGS BR rats; 40 female (156–208 g) and 40 male (198–286 g); approximately 8 weeks old were divided into 4 groups each of male and female animals as shown in Table 1, below. Animals were identified using an implanted microchip identification device encoded with a unique number. Each animal was dosed daily via oral gavage with either a test substance (R-tofisopam) or control, starting on Day 1 and through day 15. The control article was 0.5% low viscosity carboxymethylcellulose (CMC) (Lot No. 74231) and 0.4% Tween 80® (lot no. QJ1033) in reverse osmosis water.

TABLE 1

Dose group assignments for 16-day study in Rat

| Group | No. animals | Dose (mg/kg/day) | Dose concentration (mg/mL) |
|---|---|---|---|
| 1M | 10 | 0 | 0 |
| 2M | 10 | 100 | 10 |
| 3M | 10 | 200 | 20 |
| 4M | 10 | 400 | 40 |
| 1F | 10 | 0 | 0 |
| 2F | 10 | 100 | 10 |
| 3F | 10 | 200 | 20 |
| 4F | 10 | 400 | 40 |

The animals were sacrificed on Day 16 (with the exception of three males and one female which died on test or was sacrificed before the scheduled termination, and which are not included in the mean neutrophil count data). Neutrophil counts in Table 2, below, are reported as a mean value of the count for the animals of each group surviving and sacrificed on Day 16.

TABLE 2

Change in absolute neutrophil count and % change over the 16-day study.

| Group | No. animals | Mean Neutrophil count (day 16) ($\times 10^3/\mu L$) | Standard deviation ($\times 10^3/\mu L$) | Mean % change (day 16) | Standard deviation |
|---|---|---|---|---|---|
| 1M | 10 | 0.7 | 0.21 | 10 | 2.0 |
| 2M | 10 | 5.7* | 4.28 | 43* | 15.7 |
| 3M | 10 | 7.4* | 4.42 | 45* | 16.2 |
| 4M | 7 | 12.9* | 7.69 | 57* | 12.3 |
| 1F | 10 | 0.5 | 0.21 | 10 | 3.6 |
| 2F | 10 | 2.4* | 2.14 | 29* | 19 |
| 3F | 10 | 6.0* | 2.29 | 47* | 9.8 |
| 4F | 9 | 11.6* | 7.99 | 63* | 10.5 |

The normal range of absolute neutrophil counts is $0.4 \times 10^3$ cells/$\mu$L for male and $0.2$–$2.4 \times 10^3$ cells/$\mu$L for female rats. For each sex, groups 2–4 were compared with the control group (Group 1M or 1F). Group comparisons were evaluated at the 5.0%, two-tailed probability level. Data marked with * represents a statistically significant difference from the corresponding control group. Thus, this study demonstrates that neutrophil levels are significantly increased in a dose-dependant manner in the animals treated with R-tofisopam, which is a compound of formula I.

All references cited herein are incorporated by reference. The present invention may be embodied in other specific forms without departing from the spirit or essential attributes thereof and, accordingly, reference should be made to the appended claims, rather than to the foregoing specification, as indication the scope of the invention.

What is claimed is:

1. A method of increasing the absolute neutrophil count in an individual, comprising administering to said individual an effective amount of (R) -1-(3,4-dimethoxyphenyl-4-methyl-5-ethyl-7,8-dimethoxy-5H-2,3-benzodiazepine substantially free of the corresponding (S)-enantiomer, or a pharmaceutically-acceptable salt thereof.

* * * * *